United States Patent

Silver et al.

Patent Number: 5,739,286
Date of Patent: Apr. 14, 1998

[54] BONE AUGMENTATION MATERIAL

[76] Inventors: Frederick H. Silver, 103 Springbrook Dr., Bangor, Pa. 18013; David Christiansen, 270 Altamont Pl., Somerville, N.J. 08876

[21] Appl. No.: 631,818

[22] Filed: Apr. 10, 1996

Related U.S. Application Data

[60] Division of Ser. No. 524,752, Sep. 7, 1995, Pat. No. 5,532,217, which is a continuation-in-part of Ser. No. 873,366, Apr. 24, 1992, abandoned.

[51] Int. Cl.$^6$ .............. A61K 37/12; C07K 14/00; C08H 1/06; C08L 89/00
[52] U.S. Cl. .............. 530/356; 514/12; 514/21
[58] Field of Search .............. 530/356; 514/21, 514/12

[56] References Cited

U.S. PATENT DOCUMENTS

| | | | |
|---|---|---|---|
| 3,443,261 | 5/1969 | Battista et al. | 514/12 |
| 4,776,890 | 10/1988 | Cho | 514/12 |
| 5,047,031 | 9/1991 | Constanz et al. | 606/77 |
| 5,231,169 | 7/1993 | Constanz et al. | 530/356 |
| 5,532,217 | 7/1996 | Silver et al. | 514/21 |

*Primary Examiner*—Cecilia J. Tsang
*Assistant Examiner*—T. Lynn Touzeau
*Attorney, Agent, or Firm*—Louis E. Marn

[57] ABSTRACT

There is disclosed a process for the mineralization of collagen fibers whereby collagen fibers formed from collagen are contacted with a solution of calcium and phosphate ions under conditions to effect nucleation and in-vitro growth of mineral crystals within and on the surface of the collagen fibers to form intact collagen fibers with subfibrillar substructure and wherein preparations of such mineralized collagen fibers are used in bone replacement therapy as well as to induce repair in bony defects.

5 Claims, No Drawings

BONE AUGMENTATION MATERIAL

CROSS-REFERENCES TO RELATED APPLICATIONS

This is a division of application Ser. No. 08/524,752, filed Sep. 7, 1995, now U.S. Pat. No. 5,532,217, which is a continuation-in-part of U.S. Ser. No. 07/873,366, filed Apr. 24, 1992 abandoned.

BACKGROUND OF THE INVENTION

1. Field of the Invention

This invention relates to the treatment of collagen fibers, and more particularly to the mineralization of collagen fibers for use as bone replacement as well as to induce repair in bony defect.

2. Description of the Prior Art

Collagen is the major protein in animals. It has an extended history of use in the medical field primarily due to its ability to polymerize in vitro into strong fibers that can be fabricated into a number of forms. Collagen has been utilized for a variety of clinical purposes including wound treatment, hemostasis, and soft tissue augmentation. The other medical applications of collagen have been described in a recent book entitled, "Biocompatibility; Interactions of Biological and Implantable Material", Volume 1, Polymers by F. H. Silver and C. J. Doillon, VCH Publishers, New York, N.Y., 1989.

Soluble collagen has been used as a subcutaneous implant for repairing dermatological defects, such as acne scars, glabella furrows, excision scars and other soft tissue defects. Klein, A. W. J., Acad. Derm. 9:224–228 (1983); Knapp, T. R., Luck, E. and Daniels, J. R. J., Surg. Res. 23:96–105 (1977); and Kaplan, E. N., Falces, E. and Toileth, H., Clinical Utilization of Injectable Collagen, Ann. Plast. Surg., 10:437–151 (1983). Although it appears that this implant is readily accepted, the repair of thus defects is temporary and patients need additional treatment after 6 to 18 months. There were also a number of adverse tissue responses after utilization of soluble collagen. Castrow, F. F. and Kruil, E. A., Injectable Collagen Implant—Update, J. Am. Acad. Dermatol. 9:889–893 (1983). Labow, T. A. and Silvers, D. N., Late Reactions at Zydern Skin Test Sites, Cutis 35:154, 158 (1984) and Cohen, I. K., Peacock, E. E. and Chvapil, M., Editorial on Zydern. Plas. Reconstr. Surg., 73:1 (1984).

Collagen has also been used in many forms as a wound dressing. The various forms of collagen wound dressings include U.S. Pat. No. 3,157,524 and Berg et al. U.S. Pat. No. 4,320,201; and collagen/polymer film composites, such as described in McKnight et al., U.S. Pat. No. 3,800,792. However, many of these dressings are not satisfactory for the various types of full thickness wounds. Collagen films and sponges do not readily conform to varied wound shapes. Further, some collagen wound dressings have poor fluid absorption properties and enhance the pooling of wound fluids.

The use of wound dressings comprised of Type I collagen have limited commercial success because of the difficulty of the physical form of the dressing. Sponge dressings are difficult to apply to deep wounds because they do not adhere well to curved surfaces. Collagen in particulate form adheres well to wounds because of its high surface area, but is difficult to apply as dry powder because of its high surface charge. In the form of thin films, fluid absorption properties of collagen lead to pooling of fluids.

Collagen is also the structural material which forms the organic matrix of bone and is impregnated with minerals in the phosphate, hydroxyl, fluorine and carbonate ions.

OBJECTS OF THE PRESENT INVENTION

An object of the present invention is to provide a process for the mineralization of collagen fibers.

Another object of the present invention is to provide mineralized collagen for bone augmentation.

Yet another object of the present invention is to provide enhanced mineralized collagen fibers for bone healing.

Still another object of the present invention is to apply to bone site a physiologically-acceptable amount of mineralized collagen fibers.

SUMMARY OF THE INVENTION

These and other objects of the present invention are achieved by subjecting collagen fibers to nucleation and in-vitro growth of mineral crystals within and on the surface of such collagen fibers having diameters of less than about one micron to several millimeters, preferably from 20 to 500 micrometers, to form mineralized intact collagen fibers with subfibrillar substructure.

DETAILED DESCRIPTION OF THE INVENTION

Collagen fibers formed from collagen sources are placed in a container and contacted with a solution of calcium and phosphate ions at different buffered pH's to precipitate calcium phosphate. The collagen fibers are maintained for a time sufficient to effect growth of calcium phosphate crystals within and on the surface of the collagen fibers. The collagen fibers are of a diameter of from less than one micron to several millimeters, preferably with the range of from 20 to 500 micrometers, to form mineralized intact collagen fibers with subfibrillar substructure.

The mineralized collagen fibers of the present invention may be admixed with other adjuvants prior to application. The mineralized collagen fibers may be used as such as well as being formed into sheets, films, tubes, cylinders and woven knitted fabrics. The minerals containing calcium and phosphate ions can be in the form of brushite, amorphous or crystalline hydroxyapatite. In accordance with the present invention, it is essential that the collagen fibers be high purity native materials, free of potentially toxic additives which may impair tissue growth.

The mineralized collagen of the present invention in the bone dressings or implants may be admixed with a physiologically-acceptable, inert carrier. Such carriers may be a non-toxic base for forming an ointment, gel, gel cream or cream, such as, for example, petrolatum, propylene glycol, isopropyl myristate, or lanolin (for ointments); petrolatum or gelatin (for gels); or mono- and di-glycerides, ester waxes or stearyl alcohol (for creams).

Physiologically active agents, such as agents selected from the group consisting of platelet-derived growth factor, epidermal growth factor, transforming growth factor beta, angiogenesis factor, antibiotics, antifungal agents, spermicidal agents, hormones, enzymes, enzyme inhibitors and mixtures thereof may be admixed with the mineralized collagen fibers for subsequent delivery to the site. The above-mentioned agents are added to the mineralized collagen fibers in amounts varying, for example from about 1.0 to 0.1 mg per unit weight for growth factors, and 0.001 to 10 mg. per unit weight for hormones, enzymes and enzyme inhibitors.

EXAMPLE OF THE INVENTION

Reconstituted collagen fibers were prepared using the methods described by Kato et al. (Biomaterials Vol.

10:p38–42). A 1% (w/v) solution of Type I collagen in dilute HCl (pH 2.0) is blended at high speed for 4 minutes and deaerated under a vacuum to remove air bubbles. The resulting dispersion is extruded into a fiber formation buffer at 37 C. for 45 minutes. The solution is then aspirated and replaced with isopropyl alcohol for 4 hours and rehydrated with distilled water for approximately 10 minutes. The fibers are then air dried under tension. Such fibers are mineralized for a 7-day period in a double diffusion chamber. The chamber consisted of two separate reservoirs, one containing tris buffer and calcium chloride at 0.05M and 0.1M, respectively. The other reservoir contained tris buffer (0.05M) and potassium phosphate (0.1M). The ion reservoirs are separated by a small sealed tube of cellulose dialysis membrane permeable to small ions (m.s. cutoff:12,000–14,000). In the tubing, the collagen fibers are arrayed in aligned configuration. The pH of the solutions are adjusted between 5 and 10 with 6N HCl added dropwise. The solution pH tended to change as calcium phosphate precipitate is formed, thereby requiring pH measurement within the dialysis tubing at the completion of the seventh day period. The solutions are constantly stirred during the incubation. The resulting mineralized collagen fibers are air dried.

The uniaxial tensile properties of the mineralized collagen fibers are tested against controlled collagen fibers with the result that the stiffness and ultimate tensile strength of the mineralized collagen fibers being significantly increased with reference to the control collagen fibers. Scanning electron micrographs of the mineralized collagen fibers appear morphologically similar to plate-like aggregates of hydroxyapatite found precipitated on bioglass materials soaked in synthetic blood plasma.

While the invention has been described in connection with an exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

What is claimed is:

1. A bone augmentation material which comprises physiologically-acceptable mineralized intact collagen fibers with subfibrillar substructure.

2. The bone augmentation material as defined in claim 1 wherein said mineralized collagen fibers are collagen fibers having precipitated crystalline calcium phosphate on the surface thereof.

3. The bone augmentation material as defined in claim 1 wherein said collagen fibers are of a diameter of from less than 1 micron to several millimeters.

4. The bone augmentation material as defined in claim 3 wherein said collagen fibers are preferably in the range of from 20 to 500 micrometers.

5. The bone augmentation material as defined in claim 2 wherein said crystalline calcium phosphate is selected from the group consisting of brushite and hydroxyapatite.

* * * * *